United States Patent [19]
Leise, Jr. et al.

[11] Patent Number: 5,693,035
[45] Date of Patent: Dec. 2, 1997

[54] VENTED OSTOMY POUCH AND SELF-CLOSING VALVE THEREFOR

[75] Inventors: Walter F. Leise, Jr., Lindenhurst; Michael A. Metz, Chicago, both of Ill.; James J. Passalaqua, Paddock Lake, Wis.

[73] Assignee: Hollister Incorporated, Libertyville, Ill.

[21] Appl. No.: 753,202

[22] Filed: Nov. 21, 1996

[51] Int. Cl.$^6$ .................................... A61F 5/44
[52] U.S. Cl. .................. 604/333; 604/332; 128/DIG. 24
[58] Field of Search .................. 604/332–345; 128/DIG. 24

[56] References Cited

U.S. PATENT DOCUMENTS

| | | | |
|---|---|---|---|
| 3,759,260 | 9/1973 | Nolan et al. | 128/283 |
| 4,203,445 | 5/1980 | Jessup et al. | 128/283 |
| 4,274,848 | 6/1981 | La Gro | 55/387 |
| 4,449,970 | 5/1984 | Bevan et al. | 604/333 |
| 5,185,008 | 2/1993 | Lavender | 604/338 |
| 5,250,042 | 10/1993 | Torgalkar et al. | 604/333 |
| 5,401,264 | 3/1995 | Leise | 604/333 |

*Primary Examiner*—Robert A. Clarke
*Attorney, Agent, or Firm*—Tilton Fallon Lungmus

[57] ABSTRACT

An ostomy pouch is disclosed in which a flexible, shape-recoverable plastic dome is secured internally to a wall of the pouch over a vent opening. A peripheral portion of the dome spaced from the apex is provided with at least one slit therethrough traversing a radially and axially extending plane of the dome. The slit is curved or arched towards the apex and defines outer and inner lips that normally have their opposing edges in juxtaposition to restrain the escape of gases from the pouch but permit such escape in quantity when the apical portion of the dome is depressed (by axially squeezing the dome). The lips advantageously have beveled opposing surfaces with the surface of the outer lip generally facing towards the vent opening and that of the inner lip generally facing away from the vent opening. A stop element projects from the apical portion within the dome and is engagable with a deodorizing gas filter located at the base of the dome to limit the extent of deformation of the dome, and to prevent occlusion of the filter by the reverted apical portion of the dome, when the dome is pressed inwardly to open the valve.

7 Claims, 2 Drawing Sheets

VENTED OSTOMY POUCH AND SELF-CLOSING VALVE THEREFOR

BACKGROUND AND SUMMARY

U.S. Pat. No. 5,401,264 discloses an ostomy pouch with a normally-closed vent valve in the form of a slit-providing flexible dome that is secured to the interior surface of a pouch wall over a vent opening in that wall. An odor-absorbing filter extends across the vent opening to deodorize gases when they are vented from the pouch.

The slit 30 of the patented construction is centrally located, extending in linear fashion across the apical portion of the dome, and is opened when the peripheral edges of the dome are squeezed together as depicted in FIGS. 3 and 4. The squeezing forces, applied in directions generally parallel with the plane of filter 20, and from opposite ends of the slit, produces a buckling action to provide controlled venting of gases from the pouch.

While the dome functions effectively as a normally-closed relief valve that may be opened by the application of squeezing forces from generally opposite ends of the slit when venting of gases from the pouch is desired, the manipulative action required for such venting may present difficulty for the elderly and infirm, or for patients suffering from arthritis or other diseases that make it difficult to grasp the edges of the dome and apply the required squeezing forces. The problems are complicated further by the fact that such forces are not applied directly to the dome but are actually transmitted through the thin flexible walls of the pouch. The walls of such a pouch are smooth and become slippery when their surfaces are contacted by the pouch's liquid contents, so that transmitting squeezing forces through the wall of the pouch against the edges of a dome (which may not be visible through the translucent or opaque walls of the pouch), to the extent necessary to insure an opening of the relief valve, may prove difficult even for a patient of normal dexterity.

Accordingly, an important aspect of this invention is to provide an ostomy pouch, and a self-closing relief valve for such a pouch, that is considerably easier for a patient to operate when the controlled venting of gases from the pouch is desired. A further aspect of the invention is to provide a valve that is simple to operate through the application of axially-applied forces and includes means to limit the extent of flexure of the dome should excessive force be applied. The valve is therefore distinguished by being particularly user-friendly, requiring only minimal attention and dexterity for achieving the desired results.

Briefly, the relief valve embodying this invention takes the form of a flexible, shape-recovering plastic dome secured within an ostomy pouch over a vent opening formed in a wall of the pouch. In a preferred embodiment, a deodorizing gas filter extends across the vent opening. The dome is circular in outline with inner and outer surfaces most advantageously having curvatures defining portions of spheres (preferably less than semi-spherical portions).

A central apical portion of the dome is imperforate and merges smoothly with a surrounding peripheral portion. Located within the peripheral portion is at least one slit that traverses a radially and axially extending plane of the dome. The slit is curved or arched towards the apex of the dome to define a pair of curved inner and outer lips that have opposing surfaces normally in juxtaposition to restrain the escape of gases from the pouch. Such lips may be spread apart to permit such escape when the apical portion of the dome is pressed inwardly (axially) to reduce (or even reverse) the convex curvature of that portion.

The opposing surfaces of the lips are beveled and the direction of the bevel is such that the surface of the outer lip faces generally inwardly towards the vent opening whereas the surface of the inner lip faces outwardly away from the vent opening.

In a preferred embodiment of the invention, the apical portion of the dome is provided internally with stop means engagable with the deodorizing filter to limit the extent of reverse curvature of the apical portion when it is pressed inwardly to open the relief valve. In practice, such a pressing operation is performed by squeezing opposite walls of the pouch towards each other along the central axis of the dome. Since the location and curvature of the dome can easily be established by touch, and since the valve is opened by axial pressure, a venting operation may be easily performed by the fingers of one hand without requiring visual confirmation.

Other features, objects and advantages of the invention will become apparent from the specification and drawings.

DRAWINGS

DETAILED DESCRIPTION OF PREFERRED EMBODIMENTS

Figure 1:
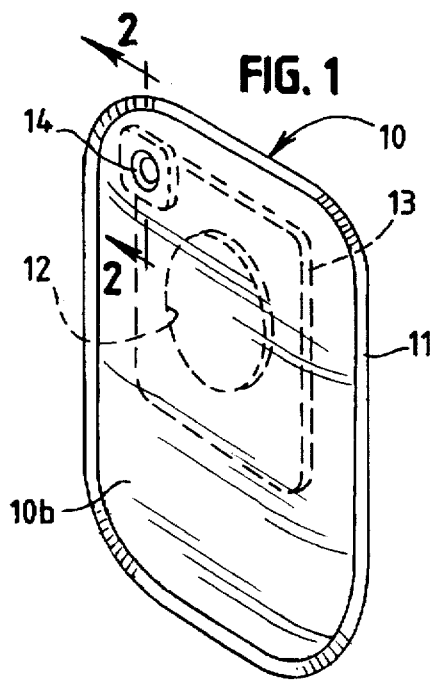
FIG. 1 is a perspective view of a vented ostomy pouch with a self-closing relief valve embodying the invention.

Referring to the drawings, the numeral 10 generally designates an ostomy pouch having a bodyside wall 10a and an obverse wall 10b joined together along their peripheral edges 11. The walls may be formed from any suitable plastic film that is strong, flexible, and fluid (gas and liquid) impermeable. Thermoplastic films capable of being heat sealed together along their edges 11 are preferred. A particularly suitable material is believed to be low-density polyethylene coextruded with polyvinylidene chloride, such material being commercially available under the designation "Saranex" from Dow Chemical, Midland, Mich. It will be understood, however, that other thermoplastic films may be used that are substantially impermeable to liquids and gases.

The bodyside wall 10a of the pouch, in accordance with standard practice, has a stoma-receiving opening 12. Attachment means are provided around that opening for securing and sealing the pouch to a patient. In the illustration given, the attachment means takes the form of an adhesive patch 13 of a type well known in the art, but it is to be understood that the attaching means might include coupling rings for detachably securing the pouch to such a patch. Where coupling rings are used, they may be constructed in accordance with the teachings of co-owned U.S. Pat. No. 5,185,008, the disclosure of which is incorporated herein by reference.

One of the walls of the pouch, preferably obverse wall 10b, is provided near its upper end with a vent opening 14. While the opening is illustrated as being circular in shape, it may if desired assume other shapes as, for example, the S-shaped configuration disclosed in U.S. Pat. No. 4,203,445. Across that opening, preferably within the interior of pouch 10, extends a deodorizing gas filter 15. The filter is shown as a subassembly composed of a flat porous filter pad 16 containing or composed of activated carbon capable of deodorizing flatus gases passing therethrough, a gas-pervious heat-sealable liquid barrier film 17, an inner cover film 18 that is gas-pervious and extends along the bodyside surface of the filter pad 16, and an outer cover film 19 along the opposite side of the pad. Film 19 is formed of gas-impervious material and has an opening 20 in register with the opening 14 of pouch wall 10b. The outer edges of films 18 and 19 are sealed together to form an envelope that encloses filter pad 16. Preferably the cover films are formed of heat-sealable materials so that they may be joined together by a peripheral heat seal 21. The same seal, or a superimposed seal, also joins the filter subassembly to pouch wall 10b in a continuous seal extending about vent opening 14. To prevent gases from bypassing the filter pad 16, film 17 is joined to cover film 19 by a heat seal 22.

Filter 15 is essentially the same as the one shown and described in U.S. Pat. No. 4,274,848, the disclosure of which is incorporated by reference herein. It is to be understood, however, that other types of deodorizing gas filters may instead be used. For example, the filter may be of the radial-flow type as disclosed in U.S. Pat. Nos. 5,401,264 and 3,759,260. Any relatively flat filter capable of being secured to pouch wall 10b across vent opening 14, and of deodorizing gases passing through that opening, may be used.

Figure 3:
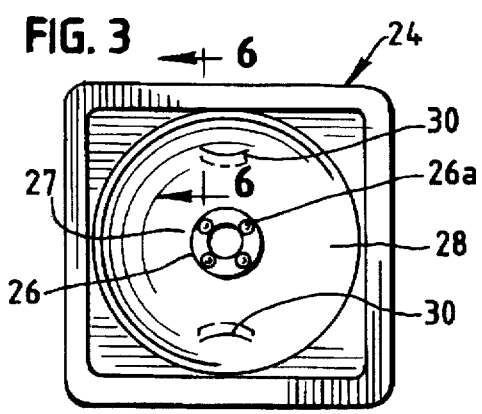
FIG. 3 is an elevational view taken from the concave side of the dome.
Figure 4:
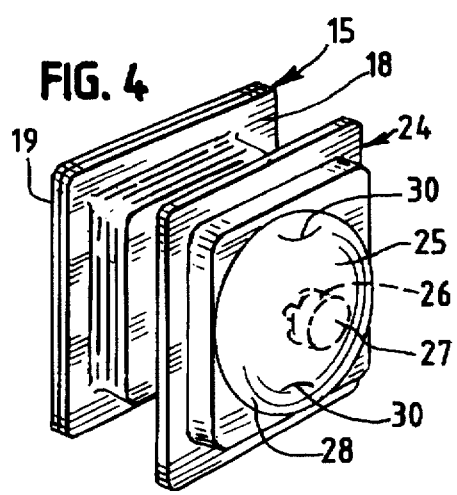
FIG. 4 is an exploded perspective view of a dome and filter.
Figure 2:
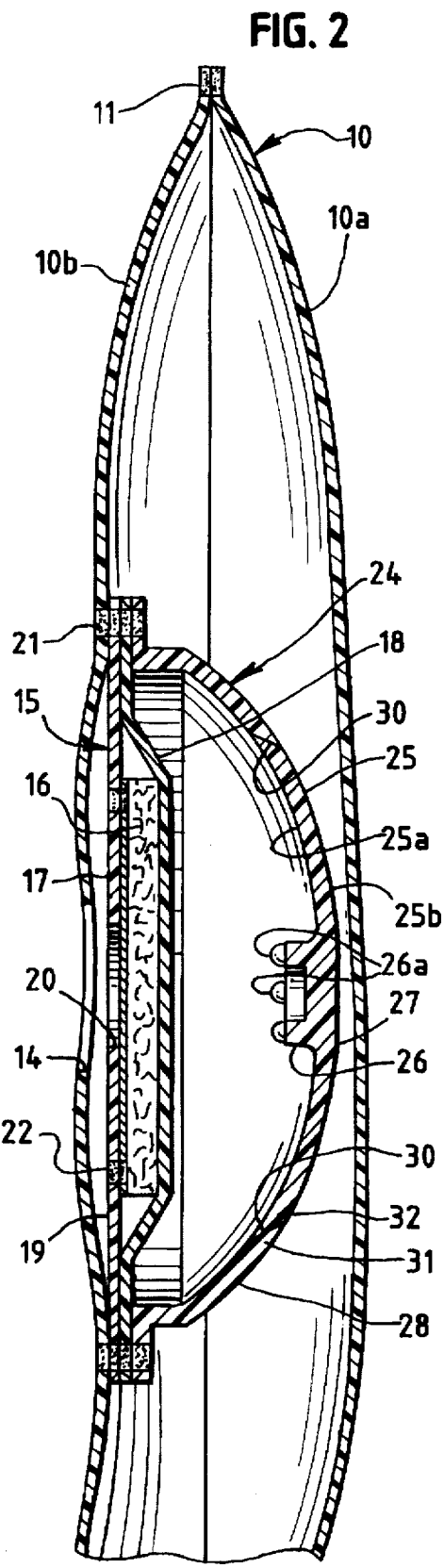
FIG. 2 is an enlarged and somewhat schematic sectional view taken along line 2—2 of FIG. 1.
Figure 5:
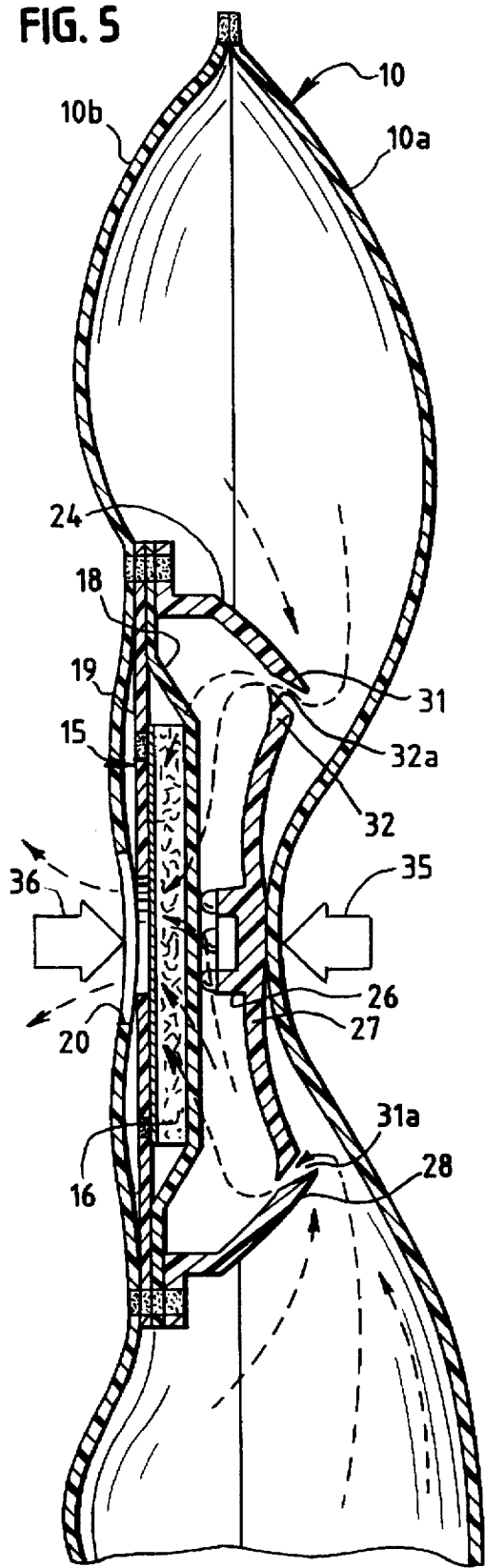
FIG. 5 is an enlarged sectional view similar to FIG. 2 but illustrating the application of forces for manually opening the relief valve.

A cover member 24 is located within pouch 10 and extends over vent 14 and filter 15. As shown most clearly in FIGS. 3 and 4, the cover member is generally square in outline, although such shape is not critical and is shown here primarily because filter 15 is also square in outline and the two elements may thus be joined together by a peripheral heat seal 21 (or by a further seal adjacent to or superimposed upon seal 21). The cover member is unitary and is formed from a flexible and shape-recoverable thermoplastic material such as, for example, low-density polyethylene or polyvinyl chloride. Any of a variety of polymeric materials which will provide a cover member that is capable of being deformed as shown in FIG. 5 and quickly recovering to its normal untensioned condition as illustrated in FIGS. 2 and 4 may be used.

The cover member 24 includes a dome portion 25 of circular outline. The dome has a concave inner surface 25a and a concentric convex outer surface 25b. Except for stop means 26 (hereinafter described), the dome is of generally uniform wall thickness. To facilitate understanding of its structure and operation, the dome may be regarded as having a central apical portion or zone 27 surrounded by a peripheral portion or zone 28, with both portions having curvatures that blend smoothly together.

Figure 6:
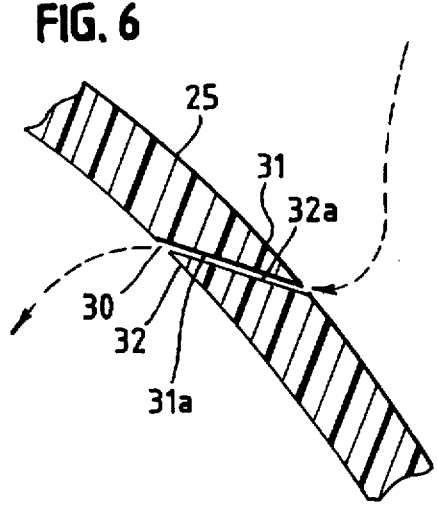
FIG. 6 is a greatly enlarged fragmentary sectional view taken along line 6—6 of FIG. 3.
Figure 7:
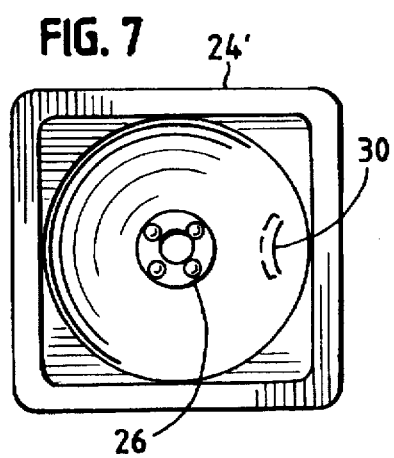
FIG. 7 is an elevational view similar to FIG. 3 but showing a second embodiment of the invention.
Figure 8:
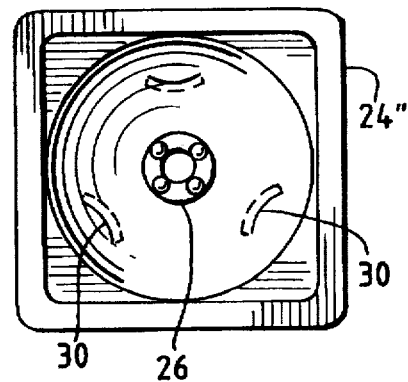
FIG. 8 is an elevational view similar to FIG. 3 but depicting a third embodiment of the invention.

Peripheral portion 28 is provided with at least one slit 30 traversing a plane that extends both axially and diametrically relative to the dome. (In FIG. 2, such plane is the plane of the paper.) Two such slits 30, diametrically disposed with respect to each other, are shown in the embodiment of FIGS. 1–6, but a lesser or greater number may be provided as indicated in FIGS. 7 and 8. When the dome is viewed in elevation, each slit is curved and defines an outer lip 31 and an inner lip 32. It will be observed from FIGS. 2 and 6 that the slit is angled to provide each lip with a beveled surface, the surface 31a of outer lip facing inwardly towards vent opening 14 and the surface 32a of inner lip 32 facing outwardly away from the vent opening.

The dome 25 operates as a self-closing relief valve in which outer lip 31 provides a relatively stationary surface and inner lip 32 acts as a valve element that is movable towards and away from the outer lip. When the apical portion 27 of the dome is pressed in the direction of the filter 15 and vent opening 14, the apical portion undergoes a deformation that partially or completely reverses the convexity of that portion and draws inner lip 32 away from outer lip 31, allowing gases that have collected within the pouch to escape through the dome and then through the filter and vent opening (FIG. 5). While the force applied to the apical portion in the direction of arrow 35 is the result of finger pressure, an opposing force is simultaneously applied in the direction of arrow 36, preferably by fingers of the same hand, as the user squeezes the two walls 10a and 10b together along the central axis of the dome. Since the location of the dome may be easily detected by touch even through the walls of the pouch, and since the valve-opening force is to be applied against the most prominent portion—the apical portion—of the dome, a user may easily open the valve to vent the pouch without visual assistance and in a manner far easier than heretofore attainable in the prior art. Upon release of the finger pressure, the deformed apical portion springs back into its original normally-closed condition (FIG. 2) to again block the discharge of flatus from the pouch.

To insure that the dome will not be excessively deformed by finger pressure and will snap back into its original condition when released, and also to prevent the reverted apical portion from occluding the filter when the dome is pressed inwardly, the apical portion 27 includes stop means 26 in the form of an integral protuberance terminating in a plurality of an annular series of rounded stop or contact elements 26a. The contact elements are arranged in a plane that is normally parallel with but spaced substantially from the opposing face of filter 15. When the walls of the pouch are squeezed together to actuate the relief valve, contact elements 26a engage the inside face of filter 15 (i.e., the surface of cover film 18 within the dome) to limit the extent of deformation of the dome.

Slits 30 are preferably formed in a die-cutting operation and it has been found that such a cutting step may tend to stretch the material along the slits beyond its limit of full recovery, with the result that, depending on factors such as the material selected, the size of the slit, and the wall thickness of the dome, the valve may be imperfect to the extent that at least some portions of the opposing lips 31a and 32a, especially portions at the ends of the slits, fail to make gas-tight sealing contact with each other when the relief valve is in its "closed" condition. While it may be possible to cut slits 30 with contact surfaces that do seal tightly against each other along the full length of the slits when the valve is closed, it has been found advantageous to intentionally create an incompetent valve so that gas at extremely low rates of flow may bleed through the closed valve and be deodorized by the vent filter while, at the same time, providing a valve that functions effectively to prevent flow at greater rates (unless the valve is intentionally opened) and protects the filter against exposure to liquids and solids contained within the pouch. FIG. 6 schematically illustrates a preferred embodiment in which opposing surfaces 31a and 32a are spaced slightly apart even though the valve is in its undeformed, closed (or substantially closed) condition.

By way of example, a valve for use in this invention may have cover member 24 formed of low density polyethylene, or a blend of low density polyethylene and ethylene vinyl acetate, with a dome thickness of approximately 0.03 inches, a dome diameter of approximately 0.94 inches, a dome radius (inside) of approximately 0.56 inches, a dome height of about 0.39 inches, and two diametrically-disposed slits, each of a length of about 0.19 inches. Tests reveal that such a dome, exposed to pressure differentials (i.e., pouch pressure over ambient pressure) over the range of 0.25 psi to 2.5 psi, will bleed gas at a rate within the range of about 0.1 to 0.5 cubic feet per hour. As previously indicated, such bleed rates may be varied by altering the length of the slit, or the number of slits, or by carefully forming the slit(s) so that the opposing surfaces of its lips make greater or lesser sealing contact when the valve is closed.

The dome-providing cover member 24' depicted in FIG. 7 is identical to the one already described except that only a single slit 30 is provided. Similarly, cover member 24" of FIG. 8 differs only to the extent that it discloses three uniformly and circumferentially spaced slits 30. The number of slits selected for any given relief valve may depend largely on the desired rate of flow through the valve when it is manually actuated as well as the desired minimum and maximum bleed rates under closed conditions.

Controllable venting of gases from the pouch 10 would be achieved even if filter 15 were absent but, in the preferred embodiments depicted in the drawings, the plastic cover member 24 with its deformable dome 25 also performs the important function of protecting a filter from contact with the liquid and solid contents of the pouch, thereby protecting the filter from becoming clogged and inoperative. The dome-shaped manually-operable relief valve therefore extends the effective life of the filter media and also allows the user to select the time and place when rapid venting of the pouch is to occur.

While in the foregoing, we have disclosed embodiments of the invention in considerable detail for purposes of illustration, it will be understood by those skilled in the art that many of these details may be varied without departing from the spirit and scope of the invention.

We claim:

1. An ostomy pouch having a pair of thin flexible side walls and having a stoma-receiving opening; a vent opening in one of said side walls for the discharge of gases from the pouch; and normally-closed valve means for normally blocking the escape through said vent opening of gases accumulating in the pouch; said valve means comprising a flexible, shape-recovering plastic dome located within said pouch and secured to said one wall over said vent opening; said dome having a central apical portion surrounded by a peripheral portion of circular outline, with both portions having outer surfaces of smoothly-blending convex curvature; said peripheral portion being provided with at least one curved slit therethrough traversing a radially and axially extending plane of said dome; said slit defining a pair of inner and outer lips normally in juxtaposition to restrain the escape of gases from said pouch but permitting such escape when said apical portion is pressed inwardly toward said vent opening to cause said lips to move apart.

2. The pouch of claim 1 in which said lips have beveled opposing surfaces; said outer lip having its beveled surface facing inwardly towards said vent opening and said inner lip having its beveled surface facing outwardly away from said vent opening.

3. The pouch of claim 2 in which said opposing surfaces of said lips have at least portions thereof that are spaced slightly apart even when said valve means is closed.

4. The pouch of claims 1, 2 or 3 in which a deodorizing filter extends across said vent opening for filtering and deodorizing gases as they are vented from said pouch.

5. The pouch of claim 4 in which said apical portion is provided with stop means engagable with said filter to limit the extent of movement of said apical portion towards said vent opening when said apical portion is pressed inwardly.

6. The pouch of claims 1, 2 or 3 in which said curved slit arches towards said apical portion of said dome.

7. The pouch of claims 1, 2 or 3 in which said peripheral portion is provided with a plurality of said curved slits in circumferentially-spaced relation to each other.

* * * * *